(12) United States Patent
Rousu et al.

(10) Patent No.: US 6,252,109 B1
(45) Date of Patent: Jun. 26, 2001

(54) METHOD FOR THE RECOVERY OF FORMIC ACID

(75) Inventors: Pasi Petteri Rousu; Juha Rainer Anttila; Esa Juhani Rousu, all of Oulu (FI)

(73) Assignee: Chempolis Oy (FI)

( * ) Notice: Subject to any disclaimer, the term of this patent is extended or adjusted under 35 U.S.C. 154(b) by 0 days.

(21) Appl. No.: 09/501,565

(22) Filed: Feb. 9, 2000

Related U.S. Application Data

(63) Continuation of application No. PCT/FI98/00635, filed on Aug. 18, 1998.

(30) Foreign Application Priority Data

Aug. 22, 1997 (FI) ........................................ 973474

(51) Int. Cl.$^7$ .................................................. C07C 51/00
(52) U.S. Cl. .............................................. 562/513; 162/76
(58) Field of Search ................................ 162/76; 562/513

(56) References Cited

FOREIGN PATENT DOCUMENTS

| 85510 | 1/1992 | (FI) . |
| 85511 | 1/1992 | (FI) . |
| WO 91/18864 | 12/1991 | (WO) . |

OTHER PUBLICATIONS

PCT International Search Report, PCT/FI98/00635, Completed Nov. 27, 1998.

*Primary Examiner*—Gary Geist
*Assistant Examiner*—Taylor V. Oh
(74) *Attorney, Agent, or Firm*—Alston & Bird LLP

(57) ABSTRACT

The invention relates to a method for removing chemically bound formic acid from a material containing the same, in the presence of free formic acid. The method is characterized in that chemically bound formic acid is allowed to react to free formic acid at a normal pressure, at a temperature of less than 100° C., the initial contact free formic acid being about 3 to 20%. The reaction time is typically 0.5 to 4 hours. The material to be treated may be, for instance, material, obtained from a formic-acid-based pulp cooking process, containing cellulose and/or lignin.

5 Claims, No Drawings

METHOD FOR THE RECOVERY OF FORMIC ACID

CROSS-REFERENCE TO RELATED APPLICATIONS

This application is a continuation of pending PCT International Application PCT/FI98/00635, filed Aug. 18, 1998, designating inter alia the United States.

FIELD OF THE INVENTION

The invention relates to a method for removing chemically bound formic acid from materials with residues of formic acid resulting from industrial chemical processes or to which the formic acid is otherwise bound. Material to be treated may be, for instance, a material containing cellulose and/or lignin. A typical material to be treated by the method of the invention is a (cellulose) pulp obtained by formic acid cooking or some other fraction recovered from a process of this kind, for instance, a lignin fraction.

BACKGROUND OF THE INVENTION

In production of formic-acid-based pulp, some formic acid remains in the pulp both in a free form and in a chemically bound form. Formic acid bound chemically to the pulp is typically in the form of a cellulose formate. Bound formic acid is also found esterified in lignin. Chemical binding of formic acid takes place particularly in connection with cooking, evaporating, distilling and drying stages. In general, chemically bound formic acid is formed in the pulp and lignin in an amount of several per cents, for instance, 3 to 5% per dry pulp unit when strong formic acid with a concentration of 60 to 100% by weight is used in cooking.

Washing with water is most generally used to remove formic acid from the pulp produced by the formic acid method. However, mere washing with water is not sufficient to remove the bound formic acid or to reduce its amount to acceptable levels. The acceptable amounts of chemically bound formic acid in a dry, unbleached pulp washed from formic acid are in the order of less than 1%, preferably less than 0.5%.

Finnish Patent 85,510 discloses a previously developed method for removing bound formic acid. This method employs vacuum evaporation at an elevated temperature, whereafter the pulp is washed with hot water or stripped with steam. The temperature used in vacuum evaporation is typically about 70 to 100° C. and in steam stripping about 100 to 140° C. In the vacuum evaporation stage the fonnic acid concentration is very high, whereby the amount of bound formic acid further increases. This bound formic acid is then removed at an elevated temperature with hot water. Drawbacks with the method are that its implementation is difficult, for instance, due to a vacuum evaporator required, and its energy efficiency is poor. High washing temperature, exceeding 100° C., also requires a special device for removing the pulp from the equipment and a unit for treating the vapours that are generated. This method requires additional investments and consumes a great quantity of energy, since the operations are carried out at higher temperatures than other process stages. Also, it is to be noted that high washing temperatures, exceeding 100° C., may have a deteriorating effect on the fibre quality, for instance, on strength properties.

The object of the method of the invention is to eliminate the drawbacks of the prior art methods and to provide a method that is useful in industrial processes for removing chemically bound formic acid without having to use high temperatures exceeding 100° C. and with using normal pressure.

SUMMARY OF THE INVENTION

The invention relates to a method for removing chemically bound formic acid from a material containing the same, in the presence of free formic acid, whereby firstly part of the free formic acid is removed by water washing from the material to be treated in order to adjust the formic acid content to a range of 3 to 20%. The method is characterized in that the chemically bound formic acid is allowed to react to free formic acid at a normal pressure, at a temperature of 50 to 95° C., the initial content of free formic acid being 3 to 20% and the reaction time being 0.5 to 4 hours, whereby free formic acid catalyzes the conversion of bound formic acid into free formic acid.

The percentages of content (%) given in the specification, examples and claims in connection with the present invention refer to percents by weight calculated on dry, brown (unbleached) pulp.

In conditions of the method of the invention, the free formic acid content being within said range of 3 to 20%, free formic acid acts as a catalyst enhancing the conversion of the bound formic acid present in esterified form into free formic acid. If the free formic acid content is too low (less than 3%) the catalyzing effect is not sufficient, whereas if the free formic acid content is too high (in excess of 20%) formulation reactions start appearing, whereby formic acid binding increases.

When treating pulp obtained from formic acid cooking, free formic acid catalyzes the hydrolyzing of cellulose formate to cellulose and free formic acid, whereby the cellulose formate in the material to be treated is completely or almost completely hydrolyzed and the formic acid in this manner removed from the pulp. When a lignin fraction is treated, free formic acid catalyzes the hydrolysis of the formic acid present in esterified form in a similar manner to free formic acid.

The starting material used in the method of the invention may originate from any chemical process utilizing formic acid, in which process organic material, such as wood, is typically used as a raw material. Typical examples are pulps obtained from a formic-acid-based pulp cooking process, or other fractions, such as a lignin fraction, containing bound formic acid and recovered from similar processes.

The starting material used in the method of the invention may also be other material to which fonnic acid is bound in esterified form.

In addition to formic acid, the material to be treated may also contain other lower carboxyl acids, such as acetic acid either in a free form or in a bound form.

When cellulose pulp is used as a starting material, it can be either softwood pulp or hardwood pulp, or as well pulp made from herbaceous plants, such as common reed or reed canary grass pulp. The material to be treated may also be pulp made e.g. from various agricultural waste materials, such as straw.

In connection with pulp making, the free formic acid acting as a catalyst in the method of the invention typically originates from the strong formic acid with a normal concentration of 60 to 100% used as a cooking chemical. The free formic acid may also originate from other processes relating to the use of fonnic acid, in which processes organic material has been treated with strong formic acid, or organic material containing formic acid has been evaporated, dried, distilled or pyrolyzed.

In practice, the 3 to 20% content of free formic acid essential to the method, is obtained by washing off part of the free formic acid with normal water washing first at a pretreatment stage. This kind of formic acid concentration can readily be arranged at the formic acid recovery stage in connection with the washing of pulp (typically counter current washing), when the pulp is in any case washed with (normally 30 to 70° C.) water. In this water washing, chemically bound formic acid cannot be removed, but it remains in the pulp typically in an amount of about 3 to 5%.

Thereafter the material to be treated, having a 3 to 20% content of free formic acid, is raised to an elevated temperature, less than 100° C., at normal pressure, whereby the free formic acid of the reaction mixture catalyzes the decomposition of the esterified formic acid to free formic acid and its removal from the material to be treated. The initial content of free formic acid is preferably 5 to 15%. The reaction temperature is 50 to 95° C., preferably 80 to 95° C. Normal pressure refers to the normal atmospheric pressure.

The short reaction time of 0.5 to 4 h is sufficient to convert the esterified formic acid to free formic acid in the conditions in accordance with the invention. The short reaction time is substantial in view of the industrial usefulness of the method.

When treating pulp, the method of the invention is in practice preferably carried out in such a way that after a pretreatment stage, in which the free formic acid content is adjusted to a range of 3 to 20%, the temperature of the material to be treated is raised to said range (less than 100° C.). The reaction mixture is allowed to stay at this temperature for the reaction time required, i.e. typically for 0.5 to 4 hours. Hence the free formic acid catalyzes the hydrolysis of cellulose fomnate to cellulose and free formic acid, whereby the cellulose formate in the material to be treated can be completely or almost completely removed therefrom. The pretreatment stage and the removal of bound formic acid are carried out arranged in connection with a commonly used multistage washing of pulp.

Correspondingly, the esterified formic acid can be released from lignin or a material containing lignin.

The method of the invention generally comprises an additional after-treatment stage, in which the formic acid released into the reaction liquid is removed from the pulp by water washing (typically at a temperature of 30 to 70° C.). Thereafter the obtained formic acid is supplied for regeneration and re-use.

In view of process technology, the chemically bound fonnic acid can be removed in a very simple manner by the method of the invention without having to use high temperatures exceeding 100° C. and complicated pressure equipment. The energy consumption of the method is low, and the effect on fibre quality is not deteriorating.

The following examples describe the method of the invention.

EXAMPLE 1

From a reed canary grass pulp, prepared in strong (85% by weight) formic acid, part of the free formic acid was first removed with water washing at a temperature of about 35° C. in such a way that the pulp contained 3.5% of free formic acid. To remove the chemically bound formic acid, the temperature of the pulp (consistency 10%) was raised to 95° C. at which the pulp was kept at normal pressure for 30 min, 1 h, 2 h and 4 h. The amount of the bound formic acid was assayed from the pulps by determining the difference between the total formic acid and free formic acid with high-resolution liquid chromatography (ionexclusion). The results of the test series are presented in Table 1.

EXAMPLES 2 AND 3

Part of the free formic acid was removed from the pulp of the same pulp batch to the effect that the pulp contained 8.6% of free formic acid. To remove the bound acid in 10% consistency, the pulp temperature was raised to 80° C. and to 95° C. respectively at normal pressure. The amount of bound formic acid was assayed from the pulps in the same manner as in Example 1. The results are presented in Table 1.

EXAMPLES 4 AND 5 (REFERENCE EXAMPLES)

The same experiment was carried out with the same pulp and in the same test itions as above, with the exception that the free formic acid content in the reaction pure was only 0.4%. The temperatures were the same as in Examples 1 to 3, i.e. 80° C. 95° C. The results are presented in Table 1.

| Example No. | Test condition | | Bound formic acid (%) at different instants of time | | | | |
|---|---|---|---|---|---|---|---|
| | Acid | Temperature | 0 min | 0.5 h | 1 h | 2 h | 4 h |
| 1 | 3.5% | 95° C. | 4.475 | 1.998 | 1.890 | 1.183 | 0.338 |
| 2 | 8.6% | 80° C. | 4.475 | 1.803 | 1.040 | | 0.0 |
| 3 | 8.6% | 95° C. | 4.475 | 1.587 | | 0.305 | 0.0 |
| 4 | 0.4% | 80° C. | 4.475 | 3.844 | 3.380 | 2.934 | |
| 5 | 0.4% | 95° C. | 4.475 | 3.334 | 3.181 | 2.866 | |

The results show that by the method of the invention the amount of bound formic acid can be reduced to acceptable levels within a time useful in industrial processes. within two hours the amount of bound formic acid can be reduced to nearly 1% or less, and within four hours the bound formic acid can be removed completely or almost completely. On the other hand, it appears from the reference examples 4 and 5 that with excessively low amounts of free formic acid, acceptable levels are not yet achieved within two hours.

In the above, the present invention is described by means of exemplary embodiments. Naturally, the invention may be modified without deviating from the scope defined in the appended claims.

What is claimed is:

1. A method for removing chemically bound formic acid from a material contacting the same, in the presence of free fonnic acid, comprising removing part of free formic acid with water washing from the material to be treated in order to adjust the free formic acid content to a range of 3 to 20%, allowing the chemically bound formic acid to react to free fonnic acid at a normal pressure, at a temperature of 50 to 95° C., and with a reaction time being 0.5 to 4 hours, such that the free formic acid catalyzes the conversion/change of the bound formic acid to free formic acid.

2. A method according to claim 1 characterized in that the reaction temperature is 80 to 95° C.

3. A method according to claim 1 characterized in that the initial content of the free formic acid is 5 to 15%.

4. A method according to claim 1 characterized in that the method further comprises an after-treatment stage, in which the released fonnic acid is removed with water washing from the material to be treated.

5. A method according to claim 1 characterized in that the material to be treated is a material, obtained from a formic-acid-based pulp cooking process, containing cellulose and/or lignin.

* * * * *

UNITED STATES PATENT AND TRADEMARK OFFICE
CERTIFICATE OF CORRECTION

PATENT NO. : 6,252,109 B1  
DATED : June 26, 2001  
INVENTOR(S) : Rousu et al.

It is certified that error appears in the above-identified patent and that said Letters Patent is hereby corrected as shown below:

Title page,
Item [73], Assignee, before "(FI)" insert -- Oulu --.

Item [57], ABSTRACT,
Line 6, "contact" should read -- content of --.

Column 4,
Line 57, "contacting" should read -- containing --;
Line 58, "fonnic" should read -- formic --.
Line 62, "fonnic" should read -- formic --.

Column 5,
Line 5, "fonnic" should read -- formic --.

Signed and Sealed this

Fifth Day of February, 2002

Attest:

JAMES E. ROGAN
*Attesting Officer*   *Director of the United States Patent and Trademark Office*